United States Patent [19]

Stice et al.

[11] Patent Number: 5,905,042
[45] Date of Patent: May 18, 1999

[54] CULTURED INNER CELL MASS CELL LINES DERIVED FROM BOVINE OR PORCINE EMBRYOS

[75] Inventors: Steven L. Stice; Paul J. Golueke, both of Belchertown, Mass.

[73] Assignee: University of Massachusetts, A Public Institution of Higher Education of the Commonwealth of Massachusetts, as Represented by its Amherst Campus, Amherst, Mass.

[21] Appl. No.: 08/626,054

[22] Filed: Apr. 1, 1996

[51] Int. Cl.$^6$ .................. A01K 67/027; C12N 15/85; C12N 15/86; C12N 5/06
[52] U.S. Cl. .................. 435/373; 435/325; 435/378; 435/379; 435/380; 435/381; 800/15; 800/17; 800/21
[58] Field of Search .................. 435/6, 7.21, 172.1, 435/172.3, 240.2, 240.21, 325, 373, 378, 404, 379, 380, 381; 425/9.1; 935/70; 800/2, 15, 17, 21

[56] References Cited

U.S. PATENT DOCUMENTS 5,523,226   6/1996   Wheeler .................. 435/240.2

FOREIGN PATENT DOCUMENTS 9003432     4/1990    WIPO .
WO 91/13150 9/1991    WIPO .
WO 94/29442 12/1994   WIPO .
WO 97/37009 10/1997   WIPO .

OTHER PUBLICATIONS

Stice et al., "Pluripotent Bovine Embryonic Cell Lines Direct Embryonic Development Following Nuclear Transfer", Biology of Reproduction, vol. 54, No. 1, Jan. 1996, pp. 100–110.

Cibelli J.B. et al., "Production of germline chimeric bovine fetuses from transgenic enbryonic stem cells", Theriogenology, vol. 47, No. 1, Jan. 1997, p. 241.

First et al, Systems for Production of Calves from Cultured Bovine Embryonic Cells, *Reproduction, Fertility, and Development*, vol. 6, pp. 553–562 (1994).

Bartlett et al, Evaluation of extracellular matrices and the plasminogen activator system in sheep inner cell mass and trophectodermal outgrowth in vitro, *Biology of Reproduction*, vol. 52, pp. 1426–1445 (1995).

Talbot et al, In vitro pluripotency of epiblasts derived from bovine blastocysts, *Molecular Reproduction and Development*, vol. 42, pp. 35–52 (1995).

Talbot et al, Culturing the epiblast cells of the pig blastocyst. *In Vitro Cellular and Development Biology*, vol. 29A, pp. 543–554 (Jul. 1993).

Annelies et al, Isolation and Characterization of Permanent Cell Lines from Inner Cell Mass Cells of Bovine Blastocysts, *Molecular Reproduction and Development*, vol. 40, pp. 444–454 (1995).

Collas et al, Nuclear Transplantation by Microinjection of Inner Cell Mass and Granulosa Cell Nuclei, *Molecular Reproduction and Development*, vol. 38, pp. 264–267 (1994).

Sims et al, Production of calves by transfer of nuclei from cultured inner cell mass cells, *Proceedings of the National Academy of Sciences, USA*, vol. 90, pp. 6143–6147 (Jun. 1993).

Seamark, R. et al (1994). Reproduction, Fertility and Development 6, 653–7.

Bradley, A. et al (1992). Bio Technology 10, 534–539.

Kappel, C. et al (1992). Current Opinion in Biotechnology 3, 548–553.

Sims, M. et al (1994). Proc. Natl. Acad. Sci USA 91, 6143–7.

Callard, R. et al (1994). The Cytokine Facts Brdc, Academic Press, pp. 163–167.

Talbot, N. et al (1993). In Vitro Cellular and Developmental Biology 29A, 543–554.

*Primary Examiner*—Brian R. Stanton
*Assistant Examiner*—Michael C. Wilson
*Attorney, Agent, or Firm*—Burns, Doane, Swecker & Mathis, L.L.P.

[57] ABSTRACT

Novel cultured inner cell mass (CICM) cells, and cell lines, derived from ungulates, in particular, pigs and cows, and methods for their preparation are provided. The subject CICMs possess similar morphology and express cell markers identically or substantially similarly to ICMs of undifferentiated developing embryos for prolonged culturing periods. Heterologous DNAs may be introduced into the subject CICM cells and cell lines to produce transgenic cells useful for the production of transgenic embryos, fetuses and/or offspring, e.g., by nuclear transfer procedures.

14 Claims, 5 Drawing Sheets

CULTURED INNER CELL MASS CELL LINES DERIVED FROM BOVINE OR PORCINE EMBRYOS

FIELD OF THE INVENTION

Novel cultured inner cell mass (CICM) cells, cell lines, and methods for their preparation are provided. The subject CICMs possess similar morphology and express cell markers identically or highly similarly to ICMs of developing embryos for prolonged culturing periods. These CICMs are produced by novel culturing techniques and/or by introduction of a regulatable differentiation inhibiting gene (DI). The subject CICM cell lines are used to produce differentiated cells, tissues, organs and/or whole animals, preferably ungulates, desirably those which have been genetically modified to contain within their genome a desired heterologous DNA or which have been selected to contain genetically desirable traits. This is accomplished by in vitro culture techniques or by producing chimeric or nuclear transfer embryos, fetuses and/or offspring. Moreover, the CICM cells can also be used for cloning (nuclear transfer procedures) to produce genetically identical embryos, fetuses and/or offspring.

BACKGROUND OF THE INVENTION

Methods for deriving embryonic stem (ES) cell lines in vitro from early preimplantation mouse embryos are well known. (See, e.g., Evans et al., *Nature,* 29:154–156 (1981); Martin, *Proc. Natl. Acad. Sci., USA,* 78:7634–7638 (1981)). ES cells can be passaged in an undifferentiated state, provided that a feeder layer of fibroblast cells (Evans et al., Id.) or a differentiation inhibiting source (Smith et al., *Dev. Biol.,* 121:1–9 (1987)) is present.

ES cells have been previously reported to possess numerous applications. For example, it has been reported that ES cells can be used as an in vitro model for differentiation, especially for the study of genes which are involved in the regulation of early development. Mouse ES cells can give rise to germline chimeras when introduced into preimplantation mouse embryos, thus demonstrating their pluripotency (Bradley et al., *Nature,* 309:255–256 (1984)).

In view of their ability to transfer their genome to the next generation, ES cells have potential utility for germline manipulation of livestock animals by using ES cells with or without a desired genetic modification. Moreover, in the case of livestock animals, e.g., ungulates, nuclei from like preimplantation livestock embryos support the development of enucleated oocytes to term (Smith et al., *Biol. Reprod.,* 40:1027–1035 (1989); and Keefer et al., *Biol. Reprod.,* 50:935–939 (1994)). This is in contrast to nuclei from mouse embryos which beyond the eight-cell stage after transfer reportedly do not support the development of enucleated oocytes (Cheong et al, *Biol. Reprod* 48:9–58 (1993)). Therefore, ES cells from livestock animals are highly desirable because they may provide a potential source of totipotent donor nuclei, genetically manipulated or otherwise, for nuclear transfer procedures.

Many research groups have reported the isolation of purportedly pluripotent embryonic cell lines. For example, Notarianni et al., *J. Reprod. Fert. Suppl.,* 43:255–260 (1991), report the establishment of purportedly stable, pluripotent cell lines from pig and sheep blastocysts which exhibit some morphological and growth characteristics similar to that of cells in primary cultures of inner cell masses isolated immunosurgically from sheep blastocysts. (Id.) Also, Notarianni et al., *J. Reprod. Fert. Suppl.,* 41:51–56 (1990) discloses maintenance and differentiation in culture of putative pluripotential embryonic cell lines from pig blastocysts. Further, Gerfen et al., *Anim. Biotech,* 6(1):1–14 (1995) disclose the isolation of embryonic cell lines from porcine blastocysts. These cells are stably maintained in mouse embryonic fibroblast feeder layers without the use of conditioned medium. These cells reportedly differentiate into several different cell types during culture (Gerfen et al., Id.).

Further, Saito et al., *Roux's Arch. Dev. Biol.,* 201:134–141 (1992) report bovine embryonic stem cell-like cell lines cultured which survived passages for three, but were lost after the fourth passage. Still further, Handyside et al., *Roux's Arch. Dev. Biol.,* 196:185–190 (1987) disclose culturing of immunosurgically isolated inner cell masses of sheep embryos under conditions which allow for the isolation of mouse ES cell lines derived from mouse ICMs. Handyside et al. (1987) (Id.), report that under such conditions, the sheep ICMs attach, spread, and develop areas of both ES cell-like and endoderm-like cells, but that after prolonged culture only endoderm-like cells are evident. (Id.)

Recently, Cherny et al., *Theriogenology,* 41:175 (1994) reported purportedly pluripotent bovine primordial germ cell-derived cell lines maintained in long-term culture. These cells, after approximately seven days in culture, produce ES-like colonies which stain positive for alkaline phosphatase (AP), exhibit the ability to form embryoid bodies, and spontaneously differentiate into at least two different cell types. These cells also reportedly express mRNA for the transcription factors OCT4, OCT6 and HES1, a pattern of homeobox genes which is believed to be expressed by ES cells exclusively.

Also recently, Campbell et al., *Theriogenology,* 43:181 (1995) in an abstract report the production of live lambs following nuclear transfer of cultured embryonic disc (ED) cells from day nine ovine embryos cultured under conditions which promote the isolation of ES cell lines in the mouse. The authors conclude based on their results that ED cells from day nine ovine embryos are totipotent by nuclear transfer and that totipotency is maintained in culture for up to three passages.

Even more recently, Campbell et al, *Nature,* 380:64–68 (1996) reported cloning of sheep by nucleic transfer from a cultured cell line. The cells used are unlike the CICM's of the present invention. Unlike the subject CICM cells, the cells of Campbell et al formed a monolayer in tissue culture. The authors refer to these cells as being "flattened" or as exhibiting an "epithelial", appearance. By contrast, the CICM cells of the present invention can be continually maintained in a multilayer colony or portions of the colony when grown in an undifferentiated state. Also, the cells of Campbell et al are cytokeratin and are laminin A/C positive. By contrast, the CICM cells of the present invention are cytokeratin negative.

Moreover, there is no suggestion that the cells of Campbell et al are undifferentiated. Rather, the reference only indicates that these cells are useful in nucleic transfer procedures. Also, these cells are not cultured under conditions wherein they maintain constant contact with a fibroblast feeder layer. Rather, the cultured cells (of Campbell et al (1996) apparently push the fibroblasts to the side in culture and grow on top of the culture dish.

Van Stekelenburg-Hamers et al., *Mol. Reprod. Dev.,* 40:444–454 (1995), reported the isolation and characterization of purportedly permanent cell lines from inner cell mass cells of bovine blastocysts. The authors isolated and cultured ICMs from 8 or 9 day bovine blastocysts under different conditions to determine which feeder cells and culture media are most efficient in supporting the attachment and outgrowth of bovine ICM cells. They concluded based on their results that the attachment and outgrowth of cultured ICM cells is enhanced by the use of STO (mouse fibroblast) feeder cells (instead of bovine uterus epithelial cells) and by the use of charcoal-stripped serum (rather than normal serum) to supplement the culture medium. Van Stekelenburg et al report, however, that their cell lines resembled epithelial cells more than pluripotent ICM cells. (Id.)

Still further, Smith et al., WO 94/24274, published Oct. 27, 1994, Evans et al, WO 90/03432, published Apr. 5, 1990 and Wheeler et al, WO 94/26889 published Nov. 24, 1994 report the isolation, selection and propagation of animal stem cells which purportedly may be used to obtain transgenic animals. Also, Evans et al., WO 90/03432, published on Apr. 5, 1990, report the derivation of purportedly pluripotent embryonic stem cells derived from porcine and bovine species which assertedly are useful for the production of transgenic animals. Further, Wheeler et al., WO 94/26884, published Nov. 24, 1994, disclose embryonic stem cells which are assertedly useful for the manufacture of chimeric and transgenic ungulates. Thus, based on the foregoing, it is evident that many groups have attempted to produce ES cell lines, e.g., because of their potential application in the production of cloned or transgenic embryos and in nuclear transplantation.

The use of ungulate ICM cells for nuclear transplantation has also been reported. For example, Collas et al., *Mol. Reprod. Dev.*, 38:264–267 (1994) disclose nuclear transplantation of bovine ICMs by microinjection of the lysed donor cells into enucleated mature oocytes. The reference discloses culturing of embryos in vitro for seven days to produce fifteen blastocysts which, upon transferral into bovine recipients, resulted in four pregnancies and two births. Also, Keefer et al., *Biol. Reprod.*, 50:935–939 (1994), disclose the use of bovine ICM cells as donor nuclei in nuclear transfer procedures, to produce blastocysts which, upon transplantation into bovine recipients, resulted in several live offspring. Further, Sims et al., *Proc. Natl. Acad. Sci., USA*, 90:6143–6147 (1993), disclose the production of calves by transfer of nuclei from short-term in vitro cultured bovine ICM cells into enucleated mature oocytes.

Also, the production of live lambs following nuclear transfer of short-term cultured embryonic disc cells (up to three passages) has been reported (Campbell et al., *Theriogenology*, 43:181 (1995)). Still further, the use of bovine pluripotent embryonic cells in nuclear transfer and the production of chimeric fetuses has also been reported (Stice et al., *Theriogenology*, 41:301 (1994)).

However, notwithstanding what has been previously reported in the literature, there still exists a significant need for cultured ICM cells and cell lines which possess improved properties, e.g., which possess morphological properties and express cell markers identically or substantially similar to ICM cells of developing embryos, in particular ungulate embryos. There further exists a significant need in the art for methods of producing such improved cultured ICM cells and cell lines.

OBJECTS OF THE INVENTION

It is therefore an object of the invention to provide novel and improved cultured inner cell mass (ICM) cells and cell lines.

It is a more specific object of the invention to provide novel and improved cultured ICM cells and cell lines which exhibit morphological characteristics and express cell markers identically or substantially similarly to that of the ICM of developing embryos.

It is an even more specific object of the invention to provide novel and improved ungulate cultured ICM cells and cell lines which exhibit morphological characteristics and express cell markers identically or substantially similarly to that of ICM of developing ungulate embryos.

It is another specific object of the invention to provide improved cultured ICM cells and cell lines, preferably derived from ungulates, which exhibit morphological characteristics and which express cell markers identically or substantially similarly to ICM of developing ungulate embryos, for prolonged culturing periods.

It is another specific object of the invention to provide novel methods for the isolation and/or production of such improved ungulate cultured ICM cells and cell lines.

It is a more specific object of the invention to provide novel methods for the isolation and/or production of cultured ungulate ICM cells or cell lines which exhibit morphological characteristics and which express cell markers identically or substantially similarly to the ICM of developing ungulate embryos, preferably for long periods in culture.

It is a specific object of the invention to provide a novel method for culturing and selecting ICM cells or cell lines which exhibit morphological characteristics and express cell markers identically or substantially similarly to ICMs of developing ungulate embryos, which method comprises:

(i) obtaining an ICM of a blastocyst or ICM progenitor cells from preblastocyst stage embryos by mechanical and/or enzymatic means;

(ii) culturing said ICM on a feeder layer culture, preferably fibroblasts; and (iii) identifying from among said cultured cells those cells which exhibit the following properties;
  (a) small cytoplasmic/nuclear volume ratio;
  (b) cytoplasmic vesicles; and
  (c) small individual cells;

(iv) separating cells having such properties from the remaining cultured cells; and (v) passaging said separated cells onto a feeder layer, preferably fibroblasts, under conditions such that the separated cells are in direct physical contact with the feeder layer.

It is a more specific object of the invention to produce improved cultured ICMs by the following steps:

(i) obtaining an ICM of blastocyst stage embryos, preferably ungulates, by suitable mechanical and/or enzymatic means;

(ii) culturing said obtained ICM onto a confluent, preferably thick, feeder cell monolayer preferably comprised of fibroblast cells;

(iii) culturing said ICM under conditions which result in a multilayer cell colony which includes a substantially inner population of flattened epithelial-like cells and a second multilayered population of cells which substantially surrounds said inner epithelial-like cells and includes relatively small cells having cytoplasmic vesicles, and small cytoplasmic/nuclear volume ratios;

(iv) separating said second multilayered population of cells which are substantially comprised on the perimeter of the multilayer cell colony by suitable non-degradative means, i.e., mechanical and/or enzymatic means; and (v) passaging said separated cells onto a new feeder layer preferably comprised of fibroblasts under conditions such that the separated cells are in direct physical contact with the feeder layer.

It is another object of the invention to provide cultured ICMs which exhibit morphological characteristics and which express cell markers identically or substantially similar to that of ICMs of developing ungulate embryos by a method comprising:

(i) obtaining ungulate ICM cells or an established cultured ungulate ICM cell line;

(ii) introducing into the nucleus of said ICM cells or said established cultured ICM cell line one or more genes which inhibit differentiation, (DI genes) which DI gene or DI genes are preferably expressed under the control of an inducible promoter;

(iii) culturing the resultant transgenic ICM cells or cultured ICM cell line on a feeder layer, preferably a confluent fibroblast layer, under conditions which provide for the expression of said differentiation inhibiting gene or genes.

It is also an object of the invention to use ICM cells or cell lines which express one or more DI genes in the above-described culturing method.

It is another specific object of the invention to use the subject improved cultured ICMs which exhibit morphological characteristics and express cell markers identically or substantially similarly to ICMs of developing ungulate embryos for any usage wherein ICMs or cultured ICMs have applicability. Such usages include, e.g., the production of differentiated cells, tissues, organs and/or whole animals by in vitro cell culture techniques or the production of chimeric or nuclear transfer embryos which may or may not be transgenic.

It is a specific object of the invention to provide cultured ICM cells which may be used in cloning (nuclear transfer procedures) to produce genetically identical ungulate embryos, fetuses and/or offspring or to produce chimeric ungulate embryos, fetuses or offspring.

It is another specific object of the invention to use the subject cultured ICMs or cell lines derived therefrom for integration of desired heterologous DNAs, and to use the resultant transgenic cultured ICMs to produce transgenic ungulate embryos, fetuses, and/or offspring or to produce transgenic chimeric ungulate embryos, and/or offspring.

DETAILED DESCRIPTION OF THE INVENTION

Figure 1:
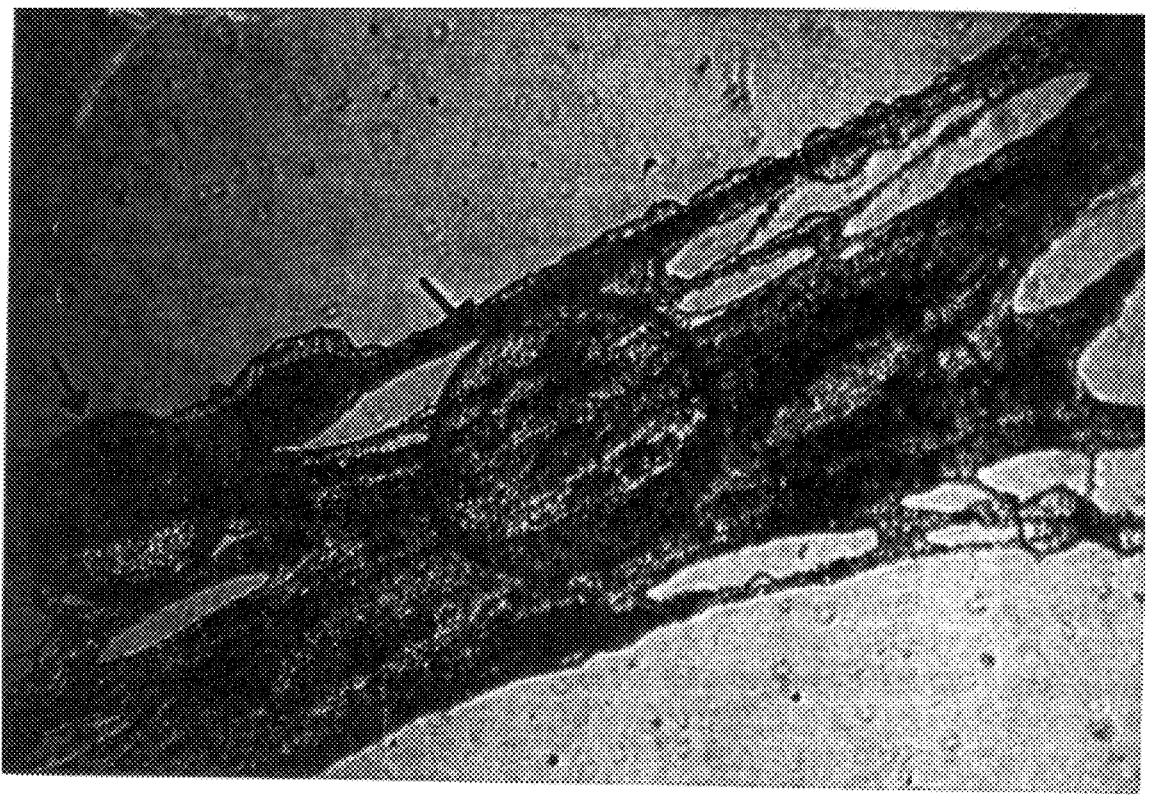
FIG. 1 is a photograph of cultured CICM cells grown without feeder layer contact. Embryoid bodies may be observed.

Prior to discussing the invention in more detail, the following definitions are provided.

Inner cell mass cells (ICM cells):

This is one of two distinct cell types which are produced during early embryonic development, i.e., the blastocyst and eventually forms part of the feeder. These cells have known application in nuclear transfer techniques, and for producing chimeric and cloned offspring.

Trophectoderm (TE cells):

This refers to the second of two distinct cell types which are produced during early embryonic development, i.e., the blastocyst stage and eventually forms part of the placenta.

ICM Progenitor cells:

These are cells comprised in pre-blastocyst stage embryos which develop into ICM cells.

Cultured inner cell mass cells:

This refers to inner cell mass cells which have been cultured in vitro for a prolonged period of time.

Cultured inner cell mass (CICM or cultured ICM) are cells which exhibit morphological characteristics and which express cell markers identically or substantially similarly to inner cell mass cells of developing embryos:

In the present invention, this will refer to cultured ICM cells which exhibit a morphology identical or highly similar to the ICM of developing embryos, e.g., ungulate embryos. In general, such cells will grow as small multilayer colonies; however, some cells may differentiate if the colony size exceeds approximately 50 to 100 cells.

CICMs which express cell markers identically to ICMs of developing ungulate embryos refers to CICM cells which express or do not express cell markers in a manner which is characteristic of undifferentiated ICMs of developing ungulate embryos. Suitable cell markers which may be used to identify suitable CICMs include by way of example cytokeratins, in particular cytokeratin 8 and cytokeratin 18, enzymes such as alkaline phosphatase, and other cell markers expressed in ICMs such as rex-1, 1 amin ac, and oct4. Ideally, the levels of expression (if any) of such cell markers will be the same as in undifferentiated ICMs obtained from ungulate embryos.

CICMs which express cell markers substantially similarly to ICMs of developing ungulate embryos refers to CICMs which express a majority of cell markers which are characteristic of undifferentiated developing ungulate ICM embryos, e.g., cytokeratins such as cytokeratin 18 and enzymes such as alkaline phosphatase, and other cell markers such as rex-1 ac and oct4. Substantially similar refers to the fact that the amount of expression of some cell markers may vary, and some cell markers may be expressed differently in the subject CICMs than in undifferentiated ICMs of ungulate embryos provided that this does not adversely affect the ability of the resultant CICMs to be cultured and maintained according to the invention.

In general, CICM cells which express cell markers identically or substantially similarly to ICMs of developing ungulate embryos will not express cytokeratin 18, and will express alkaline phosphatase. Methods for detecting the expression of such cell markers and others are known in the art (some of which are referenced infra) and include by way of example immunodetection methods. For example, such methods detect the expression or lack of expression of a particular cellular marker based on reactivity of cells with a suitable immunoprobe, e.g., a labeled antibody which provides for specific detection.

However, as discussed infra, there may be species differences in cell marker expression. (For example, whereas CICMs obtained from pigs are AP positive, CICMs obtained from cows are predominantly AP negative.) Moreover, the cultured ICMs of the present invention may also contain genes which are not normally contained in ICMs, e.g., genes which encode for a desired product and/or one or more genes which inhibit differentiation.

Differentiation inhibiting gene: In the present invention this will typically refer to any nucleic acid sequence which inhibits the differentiation of ICMs. This includes by way of example tsA58 as well as other genes encoding other T antigens and oncogene products, cytokines and transcription factors, e.g., OCT3, LIF and LIF receptor. Such differentiation inhibiting genes are known in the art and are described in WO 91/13150; Okamoto et al., *Cell*, 60:461 (1990); Rosner et al., *Nature*, 345:686 (1990); and Smith et al., *Nature*, 336:688 (1988), all of which are incorporated by reference in their entirety herein. Other suitable genes include REX-1 (Rodgers et al, *Develop.* 113:815–824 (1991)), and FGF-5 (Herbert et al, *Develop.* 112:407–415 (1991).)

Inducible or regulatable promoter:

This refers to any promoter which, when operably linked to a desired structural gene, e.g., a differentiation inhibiting gene, is "turned on", i.e., promotes transcription, under specific conditions. Typically, this requires the presence or absence of one or more substituents in the culture medium, e.g., metal ions, or other specific culturing conditions, e.g., particular temperature conditions, etc. Examples of well known inducible or regulatable promoters include by way of example response elements such as tetracycline (WO 94/29442), interferon (Kimura et al., *Cell*, 44:261 (1986)), steroid and metallothionein promoters (Yarranton, G. T., *Curr. Opin. Biotech.*, 3:506 (1992)), temperature inducible promoters, etc. These references are incorporated by reference in their entirety.

Feeder cells:

This refers to any cells which can be used to obtain and/or propagate undifferentiated cultured ICM cell lines. Preferably, such feeder cells will be fibroblasts, and more preferably murine embryonic fibroblasts, e.g., from 12–16 day old murine fetuses. Other suitable feeder cells include, e.g., fibroblast and uterine epithelial cells from ungulates, chicken fibroblasts, rat fibroblast, STO and SI-m220 feeder cell lines, and BRL cells.

Cultured multilayr ICM colony:

This refers to a growing multilayer colony of cultured ICMs on the feeder layer which exhibits a multilayer structure possessing two different, distinct cell populations. The first cell population substantially constitutes the perimeter of the multilayer cell colony and is multilayered. The cells therein include cells which are relatively small, possess cytoplasmic vesicles, and which stain strongly positive for AP activity. The other cell population is substantially comprised in the middle of the cell colony and substantially consists of a flattened epithelial-like population of cells which exhibit little or no AP activity.

As discussed, the present invention is generally directed to cultured ICM cells and cell lines which exhibit improved properties in relation to previously reported cultured ICMs. In particular, these cultured ICMs and cells exhibit morphological characteristics and express cell markers identically or substantially similarly to the ICMs of developing embryos.

The present invention provides cultured ICMs which possess a novel combination of properties which are identical or substantially similar to ICMs of developing ungulate embryos, i.e., they possess the above-defined multilayer cell colony morphology, and express cell markers identically or substantially similarly to ICMs of developing ungulate embryos, e.g., they do not express cytokeratin 18 and may or may not express alkaline phosphatase (depending on particular species of origin.)

Both the alkaline phosphatase marker and cytokeratin 18 marker have been used independently by previous researchers to determine whether cultured cells are putatively similar to developing ungulate ICMs (Piedrahita et al., *Theriogenology*, 34:879 (1990), Wheeler et al., *Reprod. Fert. Dev.*, 6:563 (1994) and Talbot et al., *Mol. Reprod. Dev.*, 36:139 (1993)). Thus, the expression of these cell markers by the CICMs produced herein provides strong evidence that the subject culturing techniques may be used to obtain ICMs which are identical or substantially similar to ICMs found in developing ungulate embryos.

This is in contrast to previously disclosed cultured ICMs, such as the cultured pig ICMs of Talbot et al (Id.) which, after culturing for only two weeks in vitro, differentiated and lost AP activity. The subject cultured ICMs are also different from the cultured bovine ICM cells of Sims et al. (Id.), which were cultured for short periods of time but which were disaggregated and grown as individual cells in a cell suspension system. The subject cultured ICMs are further different from ES-like cells which have been previously described in the literature which grow as an epithelial monolayer and which are AP negative and cytokeratin positive. Further, the subject cultured ICMs are different from those of Wheeler, *Reprod. Fert. Dev.*, 6:563 (1994) and WO 94/26884 which, while growing in multilayer colonies and being cytokeratin negative (similar to CICM cell lines of the present invention) are feeder layer independent.

Thus, the subject invention provides novel CICM cells and cell lines which, given their morphological and cell marker characteristics, should be well suited for chimera and nuclear transfer studies to produce differentiated cells, fetuses and offspring. In general, the subject novel CICM cell lines are produced by either of the following two methods.

The first method comprises obtaining ICMs of blastocyst or ICM progenitor cells from preblastocyst stage embryos, preferably those derived from ungulates. Ungulates include many important livestock animals, e.g., swine, cattle, sheep, horses and goats. Therefore, cultured ungulate cells potentially suitable for the production of ungulate animals are highly desirable. Also, ungulates afford significant advantages over other species known to be useful for production of cultured ICMs and transgenic or cloned animals, e.g., rodents, because they are immunologically and physiologically more similar to humans.

Ungulate embryos of blastocyst or preblastocyst stage may be obtained by well known methods. For example, blastocyst or preblastocyst embryos may be surgically collected from the reproductive tract of ungulates, e.g., pigs or cows, post mortem during surgical laparotomy, or non-surgically. Generally these embryos will range in age from 2 to 15 days and preferably 8 days. After collection, the ICMs of the blastocyst or preblastocyst stage ungulate embryos will either be partially separated (e.g. ICM separated from the trophoblast cells) or left intact. If partial separation is effected, it is typically effected by suitable mechanical and/or enzymatic methods, e.g., by use of a culturing glass needle and/or by incubation with trypsin or pronase.

The partially separated or intact ICMs of the blastocyst which contains the ICM and at least a portion of the trophectoderm or ICM progenitor cells derived from preblastocyst stage embryos are then introduced onto a suitable feeder cell layer culture medium. All cells derived from preblastocyst stage embryos are introduced onto a suitable feeder layer. As discussed supra, the feeder cell layer will comprise any cell layer which allows for the selection and/or propagation of undifferentiated ICMs. Preferably, the feeder cell layer will comprise fibroblasts, and more preferably those derived from primary cultures of embryonic murine fibroblasts. However, it is expected that fibroblast cell lines or other types of fibroblasts may be substituted therefor.

It has been found by the present inventors that the morphological characteristics of the feeder layer is an important factor in obtaining and propagating undifferentiated CICM cell lines in culture. More particularly, it has been found that the culture plate used for culturing the ICMs should preferably comprise a thick confluent monolayer of feeder cells, more preferably a thick confluent monolayer of murine fibroblast cells.

As discussed in greater detail in the Examples, the feeder layer is preferably obtained from primary cultures of embryonic fibroblasts, e.g., cells derived from 12–16 day old murine fetuses. Methods for the isolation of fibroblasts are well known in the art. For example, fibroblasts may be collected by aseptic removal of the head, liver, heart and alimentary tract from suitable murine fetuses, which are then minced and incubated under suitable conditions to provide for cell dissociation, e.g., incubation with a trypsin containing composition, and the dissociated fibroblasts then plated onto tissue culture dishes containing suitable culture medium.

Any medium suitable for maintaining the cultured feeder cells, e.g., murine fibroblasts, may be used. In particular, the present inventors chose to plate fibroblast cells on tissue culture dishes and culture in alpha-MEM medium (BioWhittaker, Walkersville, Md.) supplemented with 10% fetal calf serum (FCS) (Hyclone, Logen, Utah), penicillin (100 IU/ml) and streptomycin (50 $\mu$g/ml). However, it is expected that other media may be substituted therefore, including, e.g., DMEM supplemented with glutamine, glucose, 2-mercapto, ethanol, MEM non-essential amino acids, 5–20% serum, antibodies, nucleosides, glutamine (See Strojek et al, *Theriogenology* 33:981 (1990); Notarianni et al., *J. Reprod. Fert.* 43 (Suppl): 255 (1990)); and CM beta and BRL conditioned medium (See Handyside et al, *Roux's Arch. Dev. Biol.*, 196:185 (1987)).

After the fibroblasts are cultured to confluence, they are then passaged onto other tissue culture dishes or used directly for culturing of ICM cells and cell lines. Preferably, at some time after passage, and prior to introduction of a ICM, the feeder cells, e.g., fibroblasts, are also treated with an amount of an antibiotic, e.g., mytomycin C, preferably from 5 to 100 $\mu$g/ml, and more preferably about 10 $\mu$g/ml of mytomycin C, contained in a suitable culture medium, e.g., alpha-MEM or exposed to irradiation to stop or impede the growth of fibroblasts.

The feeder cells, e.g., fibroblasts are preferably cultured under conditions which allow for the production of a thick confluent monolayer of cells on the culture dishes. For example, this may be effected by maintaining the fibroblasts in a humidified atmosphere, e.g., one containing 5% $CO_2$ in air at 37° C. However, it is expected that the specific culturing conditions may be varied dependent upon factors including, e.g., the type of feeder cells, age, species, among other factors.

As discussed, culture plates which contain the desired feeder layer, preferably in the form of a thick confluent cell monolayer, are then used to obtain and culture the subject CICM cells and cell lines. This will preferably comprise plating the partially separated or intact ungulate ICMs containing at least a portion of the trophectoderm directly onto the mytomycin C treated confluent feeder layer. This is effected by any means which provides for direct physical contact between the cultured ICM and the feeder cells. This may be accomplished by different methods. For example, this may be effected by use of a glass pipette to initiate contact between the ICM and the fibroblast feeder layer. Alternatively, physical contact between feeder cell layer and cultured ICMs may be effected by placing the ICM cells under the feeder layer and the bottom of the culture dish, or by centrifuging ICM cells so as to force them onto the feeder cell layer.

The ICMs are cultured on the feeder layer using any culture medium which allows for the growth and maintenance of ICMs and the desired multilayer colony morphology. Preferably, the CICM cells or cell lines will be maintained in a growth medium consisting of alpha-MEM supplemented with FCS and 0.1 mM beta-mercaptoethanol (Sigma). However, other culture medium may be substituted therefore including, e.g., the cultured media disclosed supra.

The growth medium is exchanged for fresh medium as necessary during culturing so as to optimize cell growth. This is typically effected about every 2–3 days. However, this may vary dependent upon the specific feeder cells and the selected culture medium. After culturing is effected for several days, usually about 4 days, the first cultured ICM or CICM colonies will be observed, and some time thereafter, typically at least about 1 day later, the cultured ICMs may then be passaged onto other fibroblast feeder layer containing culture plates.

It has also been found that the passaging efficiency of CICM cells is enhanced when they are passaged together with some associated feeder cells onto a new feeder layer. Therefore, the new passage contains some of the feeder cells from the previous passage. In passaging the CICM cells together with some associated feeder cells (fibroblasts), it has been found that the passaging efficiency (percentage of CICM cell clumps which result in new colonies) is significantly enhanced.

As discussed above, an important part of the invention comprises the discovery that CICM cells comprising a particular combination of morphological properties are preferred for passaging and the production of cultured ICM cells and cell lines having the desired properties. Specifically, cells which possess the following morphological characteristics are preferred:

(i) small cytoplasmic/nuclear volume ratio (ranging from about 10/90 to about 50/50, more preferably about 10/90 to about 30/70, and most preferably about 25/75);

(ii) observable cytoplasmic vesicles; and (iii) small individual cells, ranging from about 10–20 $\mu$m in diameter, and preferably less than about 15 $\mu$m in diameter.

Calculation of cytoplasmic/nuclear volume ratios may be easily determined by observing cultured cells under the microscope, taking appropriate measurements, and making appropriate volumetric calculations. Similarly, cytoplasmic vesicles can easily be observed in cultured cells. Finally, cell size can be easily determined by measuring cell diameters of CICMs comprised on the feeder layer culture.

It has been surprisingly discovered by the present inventors that these morphological properties are important for the isolation and propagation of cultured ICM cells and the production of cell lines having the desired morphological and cell marker characteristics and which maintain such properties for prolonged periods in tissue culture, i.e., after repeated passaging.

More specifically, the present invention was based on the observation that when ICM or passaged CICM cell lines initially attach to the feeder layer, multiple layer colonies shortly become visible, typically after about 2 days. However, these multilayer colonies generally begin to flatten into epithelial sheets of cells as the cells propagate in vitro. Related to this observation, it was discovered that while the cells contained in the multilayer section of the colony are AP positive and cytokeratin 18 negative, the flattened epithelial-like cells are AP negative and cytokeratin 18 positive. Thus, the epithelial-like cells express cell markers differently from ICMs of developing fetuses. Accordingly, it was discovered that ICMs cultured on feeder cell layers over time gradually exhibit a morphology and express cell markers which are inconsistent with ICMs of undifferentiated developing embryos. This is undesirable because CICMs which exhibit properties identically or substantially similarly to undifferentiated ICMs of developing embryos will potentially be totipotent and therefore should be useful in chimeric and nuclear transfer (NT) techniques.

Thus, the goal of the present invention was to develop culturing methods which maintain or revert these ICM cell colonies such that they comprise the desired multilayered colony morphology. It was theorized, based on the described morphology of the ICM colony, that specific cells could be separated and used for passaging and that these separated cells might potentially result in the production of cultured ICMs having the desired multilayer morphology.

As noted, it was observed that the growing ICM cell colony, while initially entirely multilayer, quite rapidly flattens out to produce an epithelial sheet of cells having two distinct populations of cells within the colony. The first population is comprised on the outer perimeter of the cell colony and possesses a multilayer structure and includes cells which possess the following morphological characteristics:

(i) small cell size (cells ranging from about 10–20 $\mu$m in diameter, preferably less than 15 $\mu$m in diameter);

(ii) observable cytoplasmic vesicles; and (iii) small cytoplasmic/nuclear volume ratio (ranges from about 10/90 to about 50/50, preferably about 10/90 to about 30/70, and most preferably about 25/75.)

This outer section of the colony was also found to stain strongly positive for AP activity. By contrast, the cells in the middle of the colony tend to be comprised of flattened epithelial-like cells which exhibit little or no AP activity.

Based on the observed AP activity and multilayer structure, the present inventors decided to selectively passage only or substantially only the cells in the outer perimeter of the cell colony and specifically the cells having small cytoplasmic volume/nuclear volume ratio, observable cytoplasm vesicles and small cell size (defined supra) in the hope that these cultured cells would produce additional multilayer CICM cell colonies having the desired morphology. However, this outcome was not at all assured. To the contrary, it was possible that such passaging could have instead resulted in colonies consisting entirely of flattened epithelial-like cells, particularly if the observed epithelial-like appearance and altered cell marker expression were a consequence of culturing ICMs in vitro over prolonged time or a consequence of ICM cell passaging.

Quite surprisingly, the present inventors discovered that the selective passaging of cells comprised in the perimeter of the multilayer cell colony, possessing the above-enumerated morphological characteristics produced ICM multilayer colonies. Also, it was surprisingly found that these multilayer colonies contain cells which express cell markers identically or substantially similarly to ICM of developing embryos. Moreover, it was found that the subject method provides for the maintained production of CICMs which exhibit a morphology and express cell markers identically or substantially similarly to ICM of developing ungulate embryos, theoretically indefinitely. CICMs produced according to the invention maintain such properties for prolonged periods in culture, i.e., for at least one passage, after about 5 to 10 passages, and more preferably after about 10 to 50 passages.

The selective passaging of cells having the desired morphological characteristics may be accomplished by known cell separation methods. For example, the multilayered portion of the colony which constitutes the perimeter of the colony may be separated from the middle portion of the colony by physical means, e.g., using a glass pipette or a needle. The large cell clumps which result can then be further broken down by physical and/or chemical and/or enzymatic means. For example, cell dissociation may be effected by the use of enzymes, e.g., trypsin or pronase. Alternatively, mechanical cell separation may be effected by repeatedly pipetting large cell clusters or cell clumps through a cell pipette or by use of a needle or razor blade to cut large cell clumps into smaller groups. Preferably, such chemical and/or mechanical cell separation will produce CICM clusters suitable for passaging, i.e., which contain about 5 to 100 cells.

The separated cells used for passaging will preferably consist of cells contained in the multilayer peripheral section of the cell colony, preferably having the above-recited morphological characteristics. However, in some cases, even cells from the inner portion of the cell colony, when treated according to the invention, are found to produce multilayer colonies after passaging onto a new feeder layer.

This is believed to occur because the cells revert back to the desired multilayer colonies either because of the passaging procedure or the reestablishment of cell-to-cell contact with the new feeder layer. However, the present inventors do not wish to be bound by their belief.

During passaging, it is essential that the small ICM cells or cell clusters be placed into direct contact with the feeder layer to prevent CICM colony differentiation. It has been found that if the cells or cell clusters are grown without sufficient contact with feeder layers that this instead results in embryoid bodies. Such embryoid bodies may be observed in FIG. 1 which is a photograph showing cultured ICM cells grown without sufficient contact with a feeder layer.

To initiate direct contact, any method may be used which provides for direct cell contact between passaged CICM cells and feeder cell layer which is not degradative to the CICMs and does not adversely affect colony production. The least efficient means is to simply allow the small clumps of cells to settle down on top of the feeder layer. It is more preferable to use methods which provide for more efficient cell-to-cell contact between the CICM cells and the feeder layer. This has been found to result in a higher number of multilayer CICM cell colonies.

Any physical means which provides for enhanced physical contact between the CICM cells and the feeder cells, but which is not unduly degradative, i.e, does not adversely affect the production of the desired multilayer type cells and CICM cell lines may be used. Methods for providing for increased direct contact of passaged CICMs and the feeder layer include, by way of example, the use of a pipette to press the individual clumps of cells onto the feeder layer; the placement of CICM cell clusters under the feeder layer so that the cells are sandwiched between the feeder layer and the bottom of the dish; and the centrifugation of clumps of cells on top of the feeder layer, e.g., from between 100 and 5000 g for about 10 minutes to 5 hours to force the cell clusters onto the feeder layer. These methods are merely exemplary of methods which may be used to force the CICM cell clusters into close contact with the feeder layer. Other methods may be substituted therefore provided that they do not adversely affect the formation of the desired multilayer CICM cell colonies. As discussed above, it has also been found that passaging efficiency may further be enhanced by passaging CICM cells together with some associated feeder cells onto the new feeder colony. Apparently the presence of some of the feeder cells from the previous passage enhances the percentage of CICM cell clumps which result in new colonies.

Figure 2:
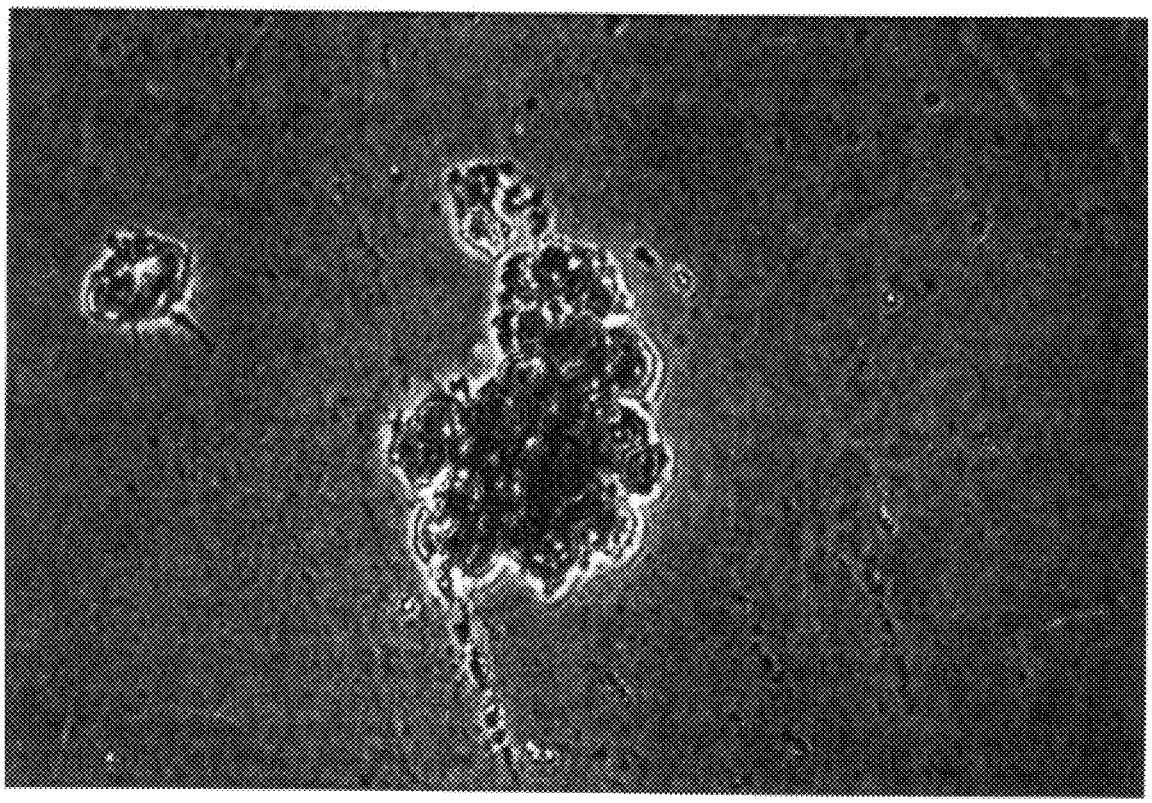
FIG. 2 is a photograph of cytokeratin positive cultured CICM cells.

In general, the above culturing procedure for culturing CICM cells is applicable to any ungulate derived CICM cells. For example, procedures initially found to be suitable for culturing pig CICM cells have been found to be applicable to bovine CICM cells. However, one observed difference is that the majority of cells derived from bovine embryos are AP negative whereas those derived from pig embryos are AP positive. It is hypothesized that there may exist species differences in AP expression in cows and pig ICMs. However, this is unclear because the inventors were able to produce one bovine cell line that was weakly AP positive and which grows in small clumps. (See FIG. 2).

Also, the bovine cells differ from the pig cells in that the borders of the colony are not as well defined. However, similar to the pig derived cells, the cells comprised in the perimeter of the colony are AP positive whereas cells in the center of the colony tend to lose AP activity. This also may be appreciated upon review of FIG. 2. Similar to pig derived CICMs, these cells are cytokeratin 18 negative.

As shown in the Examples, and described in more detail infra, the subject CICMs are useful for the introduction of heterologous DNAs. In particular, transgenic CICM cell lines have been produced which contain within their genome a heterologous DNA (beta-galactosidase DNA construct). Also, recently the inventors obtained cells using the above-described culturing methods which were somewhat different from the described CICM cells in their morphology, ability to differentiate, level of endogenous beta-galactosidase activity (higher), and ability to express beta-galactosidase DNA constructs. Moreover, these cells were AP negative from the onset of culturing, whereas previous CICM cells of pigs tended to lose AP activity over time during culturing. Similar cells have been observed and propagated in CICMs derived from cows. Although these cells lack AP activity, they exhibit some characteristics in common with ICM cells. Therefore, they may also be useful for production of transgenic cloned embryos, as well as the other described applications of CICMs.

The present invention further provides another method for providing cultured ICM cells and cell lines having the desired morphological and cell marker characteristics, e.g., CICMs which are AP positive and cytokeratin 18 negative. This second method will also involve obtaining and culturing ICMs, preferably from blastocyst or preblastocyst stage embryos of ungulates on feeder cell layer cultures. Preferably, the culturing techniques and passaging methods will be effected as described above.

However, the second method differs in the fact that the cultured ICM cells will express, preferably only under specific conditions, a differentiation inhibiting (DI) gene. This is preferably accomplished by introducing into the ICM cells, at some time during the culturing or passaging procedures, a nucleic acid sequence which includes a differentiation inhibiting gene, which is preferably expressed under the control of an inducible or regulatable promoter.

As noted above, DI genes refer to any gene or genes which may inhibit cell differentiation in the CICM cell colonies which do not adversely affect the isolation of CICM cell lines having the desired morphological characteristics and cell marker expression. The DI gene, preferably operably linked in proper reading frame to a regulatable or inducible promoter may be introduced into the nucleus of embryonic cells from which the CICM cell lines are derived during passaging, or alternatively introduced into an established CICM cell line.

This is effected in a manner which results in the DI gene, or transgene as it may be accurately described, being integrated into the genome of the embryonic ICM or cultured ICM cells or cell line. Methods for introducing desired DNAs into mammalian cells and embryonic cells in particular are known in the art and include by way of example microinjection, electroporation, lipofection, retroviral insertion, Ca precipitation, and liposome insertion. To date, microinjection appears to be the most efficient means for introducing the DNA into CICM cell lines. However, it is expected that other methods will also be effective with appropriate optimization.

Differentiation inhibiting genes suitable for use in the invention include, e.g., tsA58 (See WO 91/13150), other T antigens and oncogene products known to inhibit differentiation (See WO 91/13150 for examples thereof), OCT3 (Okamoto et al., *Cell,* 60:461 (1990), Rosner et al., *Nature,* 345:686, (1990), LIF and the LIF receptor (Smith et. al., *Nature,* 336:688 (1988)). These DI genes are merely exemplary of those which may be used in the present invention.

The DI gene is preferably placed under the control of an inducible or regulatable promoter. As noted, examples of inducible promoters are well known in the art and include by way of example the metallothionein promoter (metal ion inducible), as well as the response elements for tetracycline, interferon and steroid (See WO 94/29442; Kimura et al., *Cell,* 44:261 (1986); Yarranton, *Curr. Opm. Biotech,* 3:506 (1992)).

After the transgene is integrated into the embryonic or cultured ICM cells or cell line, and the resultant transgenic cells are established onto feeder cell cultures, the DI gene or genes are turned on by inducing the particular inducible promoter. This is typically effected by adjustment of culturing conditions. For example, if the promoter is the metallothionein promoter induction is effected by introduction of a culture medium containing appropriate metal ions which induce ("turn on") the promoter. Thereby, when the cells are cultured under induction conditions, the cultured ICM cells should continually or for prolonged periods in tissue culture maintain the desired CICM cell morphology and gene expression characteristics. More specifically, the cells should exhibit the desired multilayer cell colony morphology and express cell markers identically or substantially similarly to ICMs of developing embryos, i.e., the cells will generally be AP positive and cytokeratin (cytokeratin 18) negative. Thereby, problems such as ICM cell colonies differentiating into flattened epithelial sheets which are AP negative and cytokeratin 18 positive (which are observed when ICMs are cultured under conventional conditions) should be minimized or even eliminated. Moreover, this should also prevent the differentiation of ICM cells during passage and during sustained culture periods.

The resultant cultured ICM cells and cell lines which are obtained by the above-described methods possess numerous usages. Most especially, these CICM cell lines may be used to produce offspring which possess the CICM genetic makeup in whole or part.

Chimeric offspring may be obtained by injecting the CICM cells directly into the blastocoele cavity of recipient embryos or combined with pre-blastocyst stage embryos. The resultant chimeric embryos are then placed into a recipient female. The resultant offspring should then have a CICM genetic contribution to all organ systems including the germ cells of the reproductive organ. Thereby, the chimeric animal can pass the CICM genetics into subsequent generations of offspring. Also, the introduced CICM may have introduced in their genome a desired gene or genes. Thereby, chimeric offspring may be obtained which express a desired gene or genes. For example, genes may be introduced into CICMs which provide for enhanced livestock properties, e.g., which encode hormones, which provide for disease resistance, (e.g., lymphokines, viral resistance genes, bacterial resistance genes), enhanced milk production, altered fat percentages, enhanced body weight, among other enhanced properties. Also, genes may be introduced which encode for desired gene products, e.g., genes which encode products useful as human therapeutics or for xenotransplantation.

Also, the subject CICM cells may be used in nuclear transfer procedures to obtain nuclear transfer embryos, fetuses and offspring. Nuclear transfer techniques are known in the literature and are described in many of the references discussed in the Background of the Invention. See in particular, Campbell et al., *Theriogenology*, 43:181 (1995); Collas et al., *Mol. Reprod. Dev.*, 38:264–267 (1994); Keefer et al., *Biol. Reprod.*, 50:935–939 (1994); Sims et al., *Proc. Natl. Acad. Sci. USA*, 91:6143 (1994); Stice et al., *Theriogenology*, 41:301 (1994); Sims et al., *Proc. Natl. Acad. Sci. USA*, 90:6143–6147 (1993); WO 94/26884; WO 94/24274; and WO 90/03432 which are incorporated by reference in their entirety herein. Again, if the CICM contributes to fetal germ cells, the CICM genetics can be passed onto subsequent generations of animals. Similarly, the CICM cells may be genetically engineered such that they have integrated into their genome a desired gene or genes, e.g., genes which provide for enhanced livestock properties, or which encode for desired gene products, e.g., human therapeutics or other polypeptides.

Still further, differentiated cells, tissues or organs produced by nuclear transfer or obtained from chimeric fetuses or offspring may be used in transplantation therapies. For example, nuclear transfer or chimeric fetuses derived from CICM cells containing an anti-rejection gene or genes may provide a source of hematopoietic cells useful to supplement or replace human hematopoietic stem cells. This is potentially useful in immunocompromised patients, e.g., AIDS patients or other diseases affecting hematopoietic stem cells.

Also, stem cells may be useful in treatment of Huntington's disease, Parkinson's disease and Alzheimer's disease. Moreover, pancreatic cells may be useful in diabetes treatments. Further transplanted liver cells may be useful for the treatment of liver diseases. Alternatively, whole soft organs may potentially be transplanted from genetically altered CICM-derived ungulates into humans (See Durling et al., *Curr. Omp. Immunol.*, 6:765 (1994)) incorporated by reference in its entirety herein.

Also, the subject CICM cell lines may be used as an in vitro model of differentiation, in particular for the study of genes which are involved in the regulation of early development.

This is only exemplary of potential applications of CICM cell lines obtained according to the present invention.

The invention will now be described in more detail in the following Examples.

EXAMPLE 1

Production of CICM cell lines from pre-blastocyst and blastocyst stage pig embryos were conducted using the following general protocol. First, primary cultures of embryonic fibroblasts were obtained from 12–16 day old murine fetuses. After the head, liver, heart and alimentary tract were aseptically removed, the embryos were minced and incubated for 30 minutes at 37° C. in prewarmed trypsin EDTA solution (p.05% trypsin/0.02% EDTA; GIBCO, Grand Island, N.Y.). Fibroblast cells were plated in tissue culture dishes and cultured in alpha-MEM medium (BioWhittaker, Walkersville, Md.) supplemented with 10% fetal calf serum (FCS) (Hyclone, Logen, Utah) penicillin (100 IU/ml) and streptomycin (50 μg/ml). Three to four days after passage, embryonic fibroblasts, in 35×10 Nunc culture dishes (Baxter Scientific, McGaw Park, Ill.), were treated with mitomycin C (10 μg/ml; Sigma) in supplemented alpha MEM for a minimum of three hrs. The fibroblasts were grown and maintained in a humidified atmosphere with 5% $CO_2$ in air at 37° C. Only culture plates which had a thick confluent monolayer of cells were used to culture the CICM cell lines. The characteristics of the feeder layer is an important factor in obtaining and propagating undifferentiated CICM cell lines.

Porcine embryos were surgically collected from the reproductive tract post mortem or during surgical laparotomy. The ICM of blastocyst stage embryos were either partially separated from the trophoblast cells using a cutting needle, incubated in trypsin or pronase, or left intact. The ICM and at least a portion of the trophectoderm was plated directly onto the mitomycin C blocked fibroblast cells often using a glass pipette to initiate contact between the ICM and the fibroblast feeder layer. The CICM cell lines were maintained in a growth medium consisting of alpha MEM supplemented with 10% FCS and 0.1 mM beta-mercaptoethanol (Sigma). Growth medium was exchanged every two to three days. Initial colonies were observed by the fourth day of culture and could be passaged any time after the fifth day. Only cells having the following three morphological features were isolated for passage: a small cytoplasmic/nuclear volume ratio, cytoplasmic vesicles, and generally small individual cells (less than 15 μm in diameter). These cells are often isolated from multilayer portions of the colony which maintained direct contact with the feeder layer. The portions of the colony that met this criteria were often AP positive and cytokeratin negative upon passage onto a new feeder layer.

Figure 3:
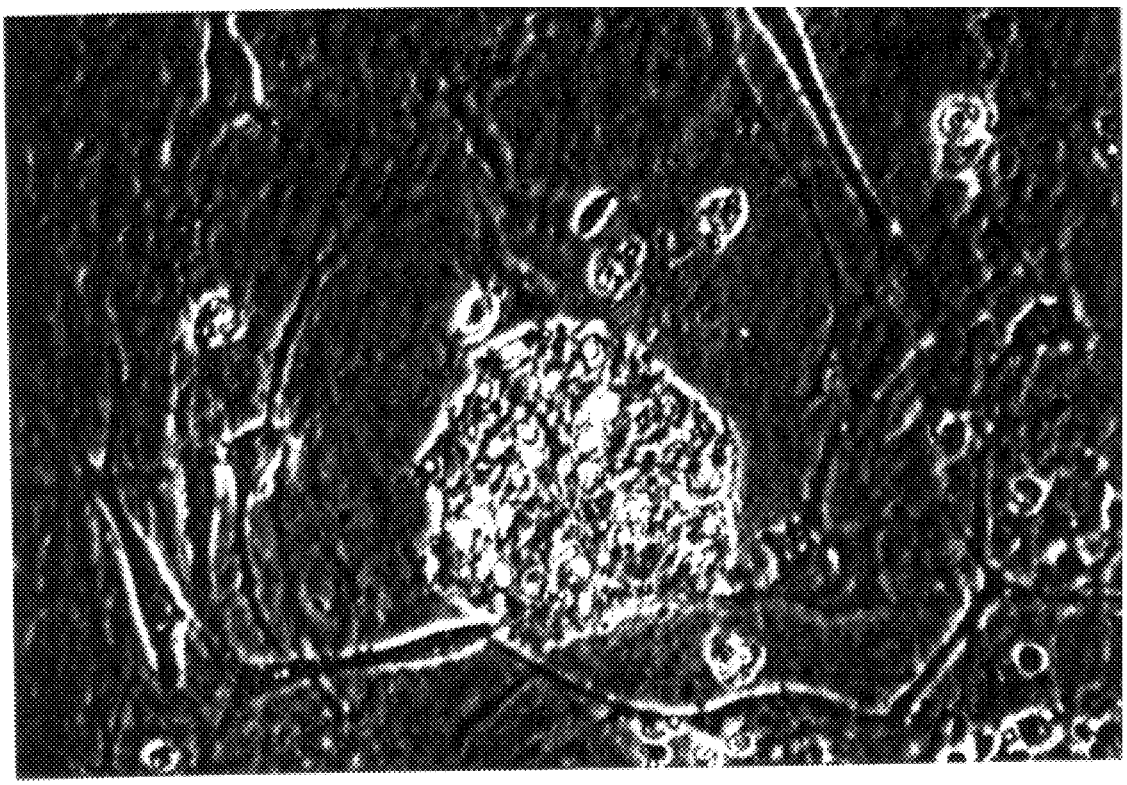
FIG. 3 is a photograph of CICM cells on a fibroblast feeder layer. Multiple layer colonies are visible after only 2 days of culturing.
Figure 4:
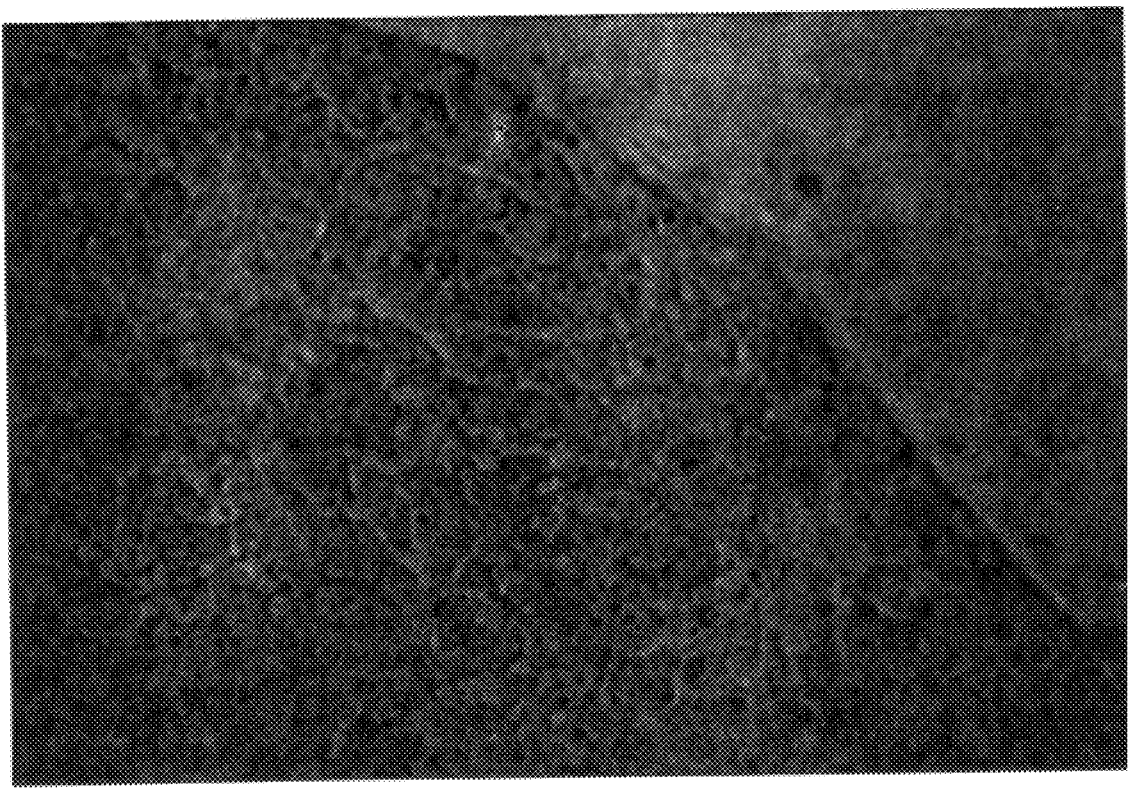
FIGS. 4 and 5 are photographs showing AP positive and cytokeratin negative CICM cell colonies.
Figure 5:
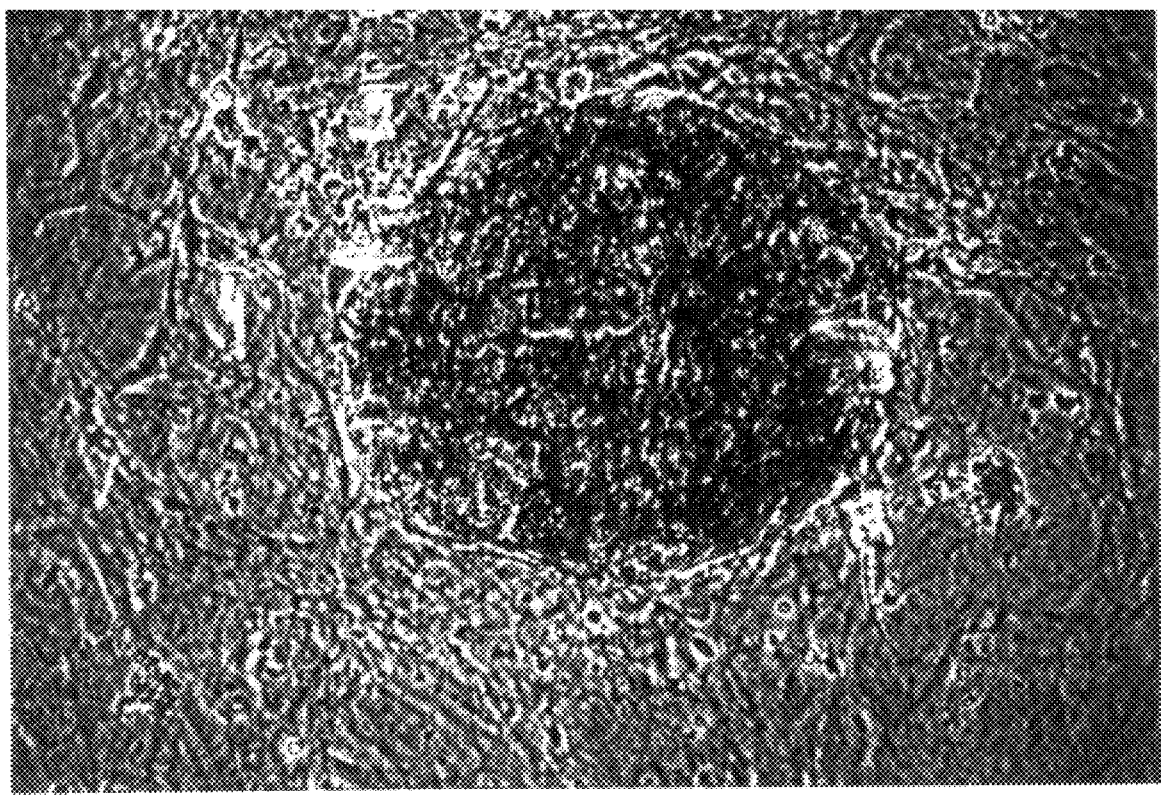
Figure 6:
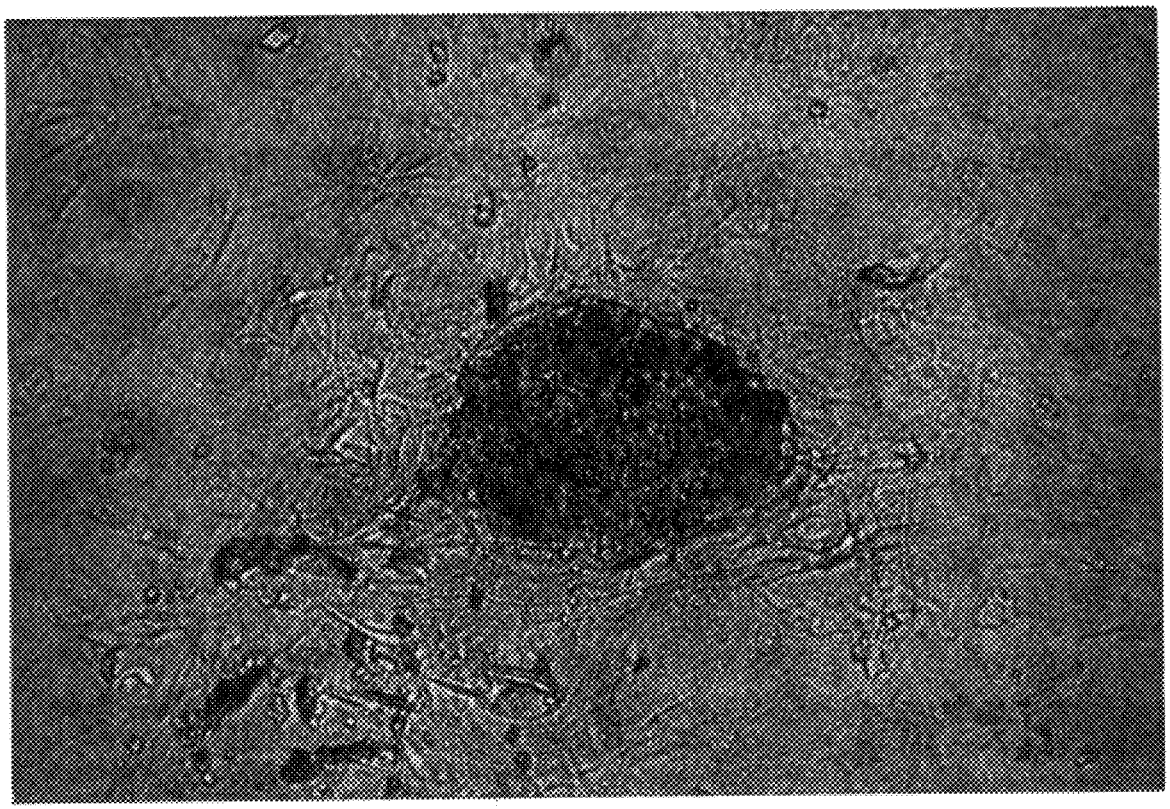
FIGS. 6 and 7 are photographs showing epithelial-like cells which are obtained during culturing of CICM cells. Those cells are AP negative and cytokeratin positive.
Figure 7:
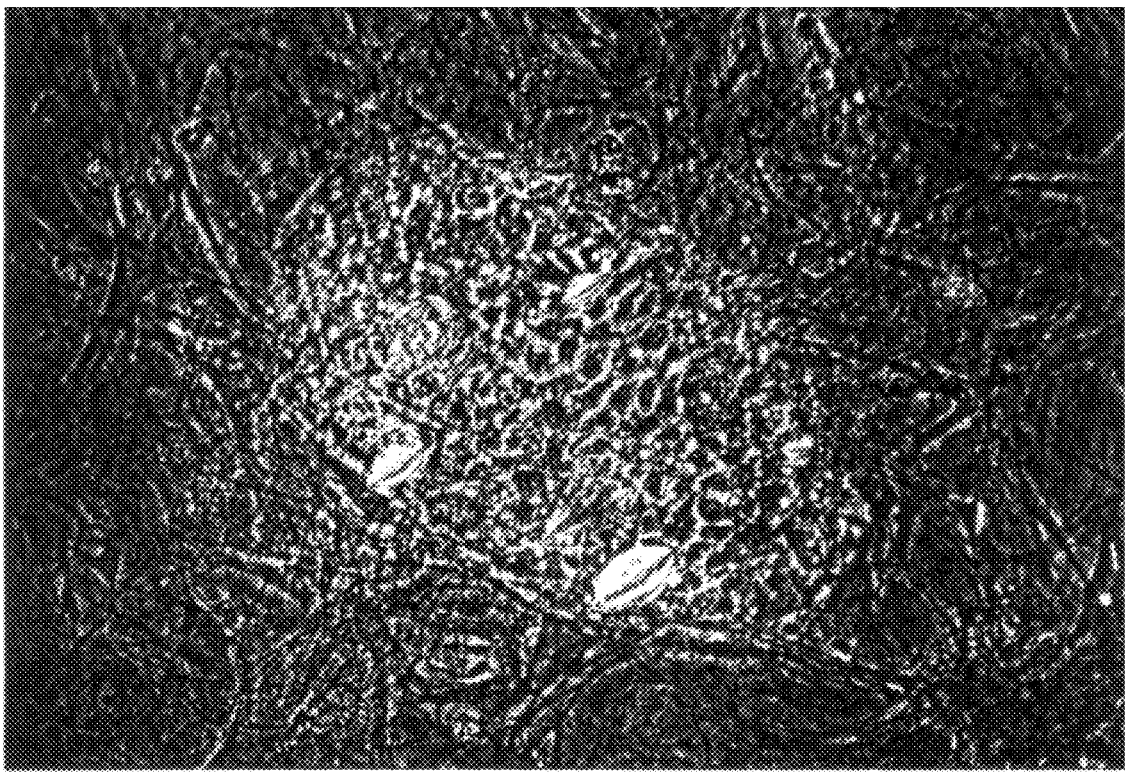
Figure 8:
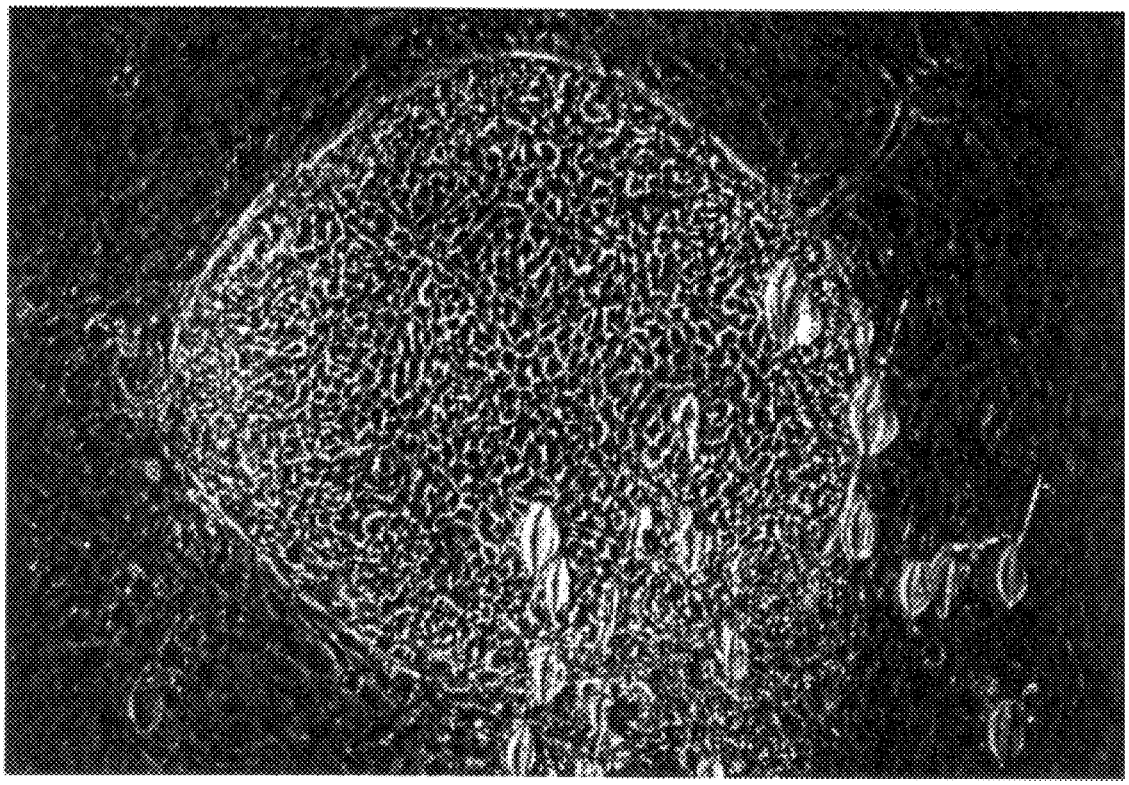
FIG. 8 is a photograph of CICM cell colonies. This photo shows that multilayer colonies are beginning to flatten into epithelial-like cell sheets. The cells in the middle of the colony are AP negative and exhibit a flattened epithelial-like appearance. By contrast, cells in the perimeter are smaller, exhibit a multilayered morphology and possess cytoplasmic vesicles.

When the ICM or the passaged CICM cells initially attach to the feeder layer, multiple layer colonies consisting of small cells are visible after two days in culture. This can be seen in FIG. 3. The multilayer colonies are AP positive and cytokeratin negative (See FIGS. 4 and 5). However, some of the colonies begin to form an epithelial-like sheet of cells. The epithelial-like cells are AP negative and cytokeratin positive (FIGS. 6 and 7). In addition, the multilayer colonies often begin to flatten into epithelial sheets of cells as they propagate in vitro (FIG. 8).

It was observed by the inventors that a growing multilayer colony begins to flatten out, forming an epithelial sheet of cells having two distinct populations of cells within the colony. The first population resides in an area around the perimeter of the colony. This section of colony is multilayered and the individual cells are small and possess cytoplasmic vesicles (FIG. 8). This area also stains positive for AP activity. The other area of the colony contains the flattened epithelial-like population of cells. These cells tend to be in the middle of the colony. In this population of cells, individual cells and cell borders can be observed when viewing the colony under a microscope (FIG. 8). Again, these cells have very little AP activity or none at all.

It was theorized that to maintain the desired multilayer type cells, preferably, only the cells around the perimeter would be selectively passaged to produce additional multilayer colonies.

This is probably accomplished by using a glass pipette razor or a needle to cut out the multilayer portions of the colony (perimeter cells). The large groups of cells can be broken down further either by mechanical separation or by using trypsin (0.05% trypsin/0.2% EDTA) along with the mechanical separation. Mechanical separation is conducted by repeatedly pipetting large clumps of cells up and down through a small bore pipette. Alternatively, a needle or razor blade can be used to cut the large group of cells into smaller groups. It was surprisingly found that CICM clumps obtained by all these methods (5 to 100 cell) can then be passaged onto new feeder layers to produce cultures having the desired multilayer morphology. In some occasions even cells from the inner portion of the colony when treated in this same manner, produced multilayer colonies after passage onto new feeder layers. It is hypothesized that these cells reverted back to the multilayer colonies as a result of either the passage procedure or the reestablishment of cell to cell contact with the new feeder layer.

It was observed that the small clumps of cells must be placed back in direct contact with the feeder layer to prevent CICM colony differentiation. By contrast, cells grown without contact with feeder layers form embryoid bodies (FIG. 1). There are several methods used to reinitiate feeder layer contact. The least efficient means is to allow the small clumps of cells to settle down on top of the feeder layer after the cell culture plates are placed back in the incubator. A preferred method involves forcing cell to cell contact between the CICM cells and the feeder layer. This results in a higher number of newly established CICM cell colonies. One way to force cell to cell contact is to use a pipette to press the individual clumps of cells down on top of the feeder layer. Another method is to place the clump of CICM cells under the feeder layer so that the cells are forced between the feeder layer and the bottom of the culture dish. Still alternatively, clumps of cells on top of the feeder layer can be centrifuged between (100 and 5000 g) for (10 min to 5 hrs) to force the cells down on top of the feeder layer. Essentially, any method which forces the passaged clumps of CICM cells into close contact with the feeder layer results in the production of CICM cell colonies having the desired multilayer morphology. Also, as discussed previously, passaging efficiency may be further enhanced by passaging CICM cells along with some associated feeder cells onto the new feeder layer.

EXAMPLE 2

CICM cells obtained according to Example 1 were used for insertion of heterologous DNA's. Specifically, these cells were microinjected with linear as well as supercoiled DNA constructs containing different promoters placed in front of either the beta-galactosidase gene and/or the neomycin phosphotransferase gene. The specific promoters used were the cytomegalovirus promoter (CMV promoter), phosphoglycerate Kinase promoter (PGK promoter), mammary promoter (MAM promoter), reCMV promoter and chicken beta actin promoter. These gene constructs were diluted in a buffered solution (containing 80 mM KCl and 70 mM HEPES.) However, other buffers may readily be substituted therefore, such as Tris EDTA. The concentration of the DNA constructs in solution ranged from 5 to 10 $\mu$g/ml. However, concentrations ranging from 0.1 to 100 $\mu$g/ml should be effective. These DNA preparations were then microinjected into cultured CICM cells obtained according to Example 1.

In this procedure, the individual CICM cells within the colonies were located by viewing the colonies through an inverted microscope. Thereafter, the cell membrane alone or additionally the nuclear membrane was punctured using a small injection needle containing the DNA preparation. The opening in the needle was about 1 $\mu$m. Such a diameter needle was selected to help prevent CICM cell lysis. Moreover, the microinjection procedure was facilitated by the use of a micromanipulator which was attached to the inverted microscope.

After the injection pipette was introduced into the nucleus, approximately 700 copies of the DNA were released into the nucleus. The micropipette was then removed from the cell. This process was repeated for other cells in the CICM colony. Ideally, 1000 cells may be microinjected per hour.

The results obtained using the different promoters are summarized in the following table.

| Heterologous Gene Expression in Microinjected CICM Cells | | |
|---|---|---|
| promoter | expression two hours after injection | expression five days after injection |
| CMV | +++ | ++ |
| PGK | ++ | none |
| reCMV | ++ | not tested |
| MAM | ++ | not tested |
| C-Actin | + | not tested |

The above results demonstrate that vectors containing each of the tested promoters result in cells which express the inserted heterologous DNA. It was also observed that microinjection with several constructs did not provide for any additive effects on gene expression.

Figure 9:
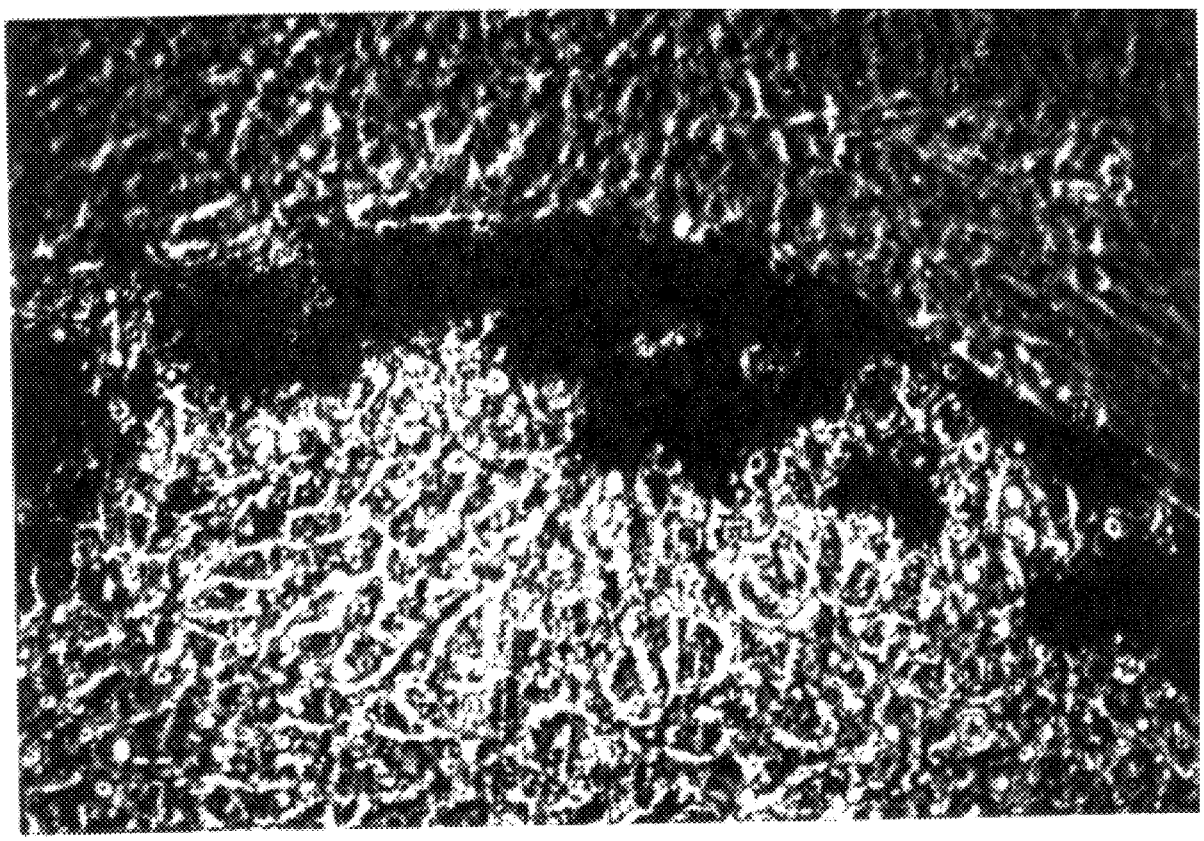
FIG. 9 is a photograph showing cultured pig CICM cells expressing a beta-galactosidase DNA construct five days after microinjection.

FIG. 9 is a photograph of microinjected pig CICM cells containing a CMV beta-galactosidase construct detected by X-gal staining. Nests of cells expressing b-galactosidase may be seen. This indicates that the β-galactosidase gene has been effectively incorporated into the cell genome and is being transmitted and expressed in daughter cells.

The above results were obtaining using pig CICM cells. Moreover, using similar methods, bovine CICM cells were also injected with CMV and PGK-beta-galactosidase constructs. Both DNA constructs resulted in recovery of cells which express beta-galactosidase.

Thus, these results demonstrate that CICM's cultured according to the invention may successfully be used for integration and expression of desired heterologous DNA's. Also, these gene expression characteristics may be passed onto daughter cells.

EXAMPLE 3

In this culturing method, a DI gene is conditionally expressed in CICM cell colonies to prevent cell differentiation. The cell passage and culture techniques are the same as in Example 1 with the difference being the genetic makeup of the CICM cells. Specifically, a DI gene is introduced into the nucleus of embryonic cells from which the CICM cell lines are derived or into an established CICM cell line. The transgene is then integrated into the genome of the CICM cells. Any known methods of introducing transgenes into embryonic cells can be used, including by way of example microinjection, electroporation, retroviral insertion, Ca precipitation, and liposome insertion.

The inserted transgene is expressed under the control of an inducible promoter. Inducible promoters include, e.g., response elements such as tetracycline (WO 94/29442), interferon (Kimura et al., 1986), steroid and metallothionein (reviewed by Yarranton, 1992). Accordingly, the DI gene is inserted such that it is operably linked, in proper reading frame, with an inducible promoter.

After the chimeric gene construct is integrated into the genome of the embryonic cells and the multilayer ICM cell colony is established, the DI gene is expressed by inducing the inducible promoter. This expression provides for the ICM cell colony to continuously, or for prolonged time in tissue culture, maintain the desired multilayer morphology and to express genes consistent with ICM of developing embryos. Thus, problems such as cells differentiating into flattened epithelial sheets that lose their AP expression and express cytokeratin 18 are minimized or even avoided altogether. This method is also useful in preventing differentiation of cells during long term culture periods.

While the invention has been described with respect to certain specific embodiments, it will be appreciated that many modifications and changes thereof may be made by those skilled in the art without departing from the spirit of the invention. It is intended, therefore, by the appended claims to cover all modifications and changes that fall within the true spirit and scope of the invention.

What is claimed is:

1. A method for producing a bovine or porcine cultured inner cell mass (CICM) cell which may be incorporated into a bovine or porcine embryo to form a chimeric bovine or porcine which consists essentially of the following steps:

(i) obtaining inner cell mass (ICM) cells from a bovine or porcine blastocyst or ICM progenitor cells from a bovine or porcine preblastocyst stage embryo;

(ii) culturing said ICM or ICM progenitor cells on a feeder layer culture to produce multilayer cell colonies;

(iii) identifying from among the cells contained in the cultured ICM or ICM progenitor cell colony those cells which exhibit the following properties:
  (a) small cytoplasmic/nuclear volume ratio ranging from about 10/90 to 50/50;
  (b) cytoplasmic vesicles;
  (c) small individual cells ranging from about 10 to 20 $\mu$m in diameter;

(iv) separating one or a cluster of said identified cells from the rest of the cell colony; and (v) passaging said separated ICM or ICM progenitor cells onto another feeder layer culture and maintaining physical contact between the feeder cell layer and the separated cell or cell cluster throughout the entire culturing period to produce CICM cells that may be incorporated into a bovine or porcine embryo to form a chimeric bovine or porcine.

2. The method of claim 1 wherein said ICM obtained in step (i) includes a portion of the trophectoderm.

3. The method of claim 2 wherein the cells are less than 15 microns in diameter.

4. The method of claim 1 wherein the feeder cell layer contains fibroblasts.

5. The method of claim 4 wherein said fibroblasts are murine embryonic fibroblasts.

6. The method of claim 5 wherein said murine embryonic fibroblasts are primary cells.

7. The method of claim 4 wherein said fibroblast containing feeder layer is a confluent monolayer.

8. The method of claim 1 wherein physical contact of the separated cells of step (iv) and the feeder cell layer is maintained by a means selected from the group consisting of (i) placing the separated ICM cells on top of the feeder cell layer, (ii) pressing CICM cell clusters onto the feeder layer, (iii) placing CICM cell clusters between the feeder cell layer and the culture dish, and (iv) centrifuging the CICM cells or cell cluster onto the feeder cell layer.

9. The method of claim 1 wherein the identified cells are separated from the colony by at least one of the following means: physical, chemical or enzymatic means.

10. The method of claim 9 wherein said physical means comprises physically contacting the colony with a glass pipette, hypodermic needle or razor blade.

11. The method of claim 10 which further comprises treatment of said separated cells with trypsin or pronase.

12. The method of claim 1 wherein the separated cells contain a cluster of about 5 to about 100 cells.

13. The method of claim 1 wherein steps (ii) through (v) are repeated.

14. The method of claim 1 wherein said ratio is about 25/75.

* * * * *